United States Patent
Cobb et al.

(10) Patent No.: US 10,364,427 B2
(45) Date of Patent: Jul. 30, 2019

(54) METHOD OF DNA/RNA EXTRACTION USING SILYATED QUATERNARY AMMONIUM COMPOUNDS (SIQAC)

(71) Applicant: ARCIS BIOTECHNOLOGY HOLDINGS LIMITED, Daresbury, Warrington Cheshire (GB)

(72) Inventors: Benjamin David Cobb, North Wraxall (GB); Jan Rogers, Chester (GB)

(73) Assignee: ARCIS BIOTECHNOLOGY HOLDINGS LIMITED, Daresbury, Warrington Cheshire (GB)

( * ) Notice: Subject to any disclaimer, the term of this patent is extended or adjusted under 35 U.S.C. 154(b) by 763 days.

(21) Appl. No.: 14/779,660

(22) PCT Filed: Mar. 24, 2014

(86) PCT No.: PCT/GB2014/050923
§ 371 (c)(1),
(2) Date: Sep. 24, 2015

(87) PCT Pub. No.: WO2014/155078
PCT Pub. Date: Oct. 2, 2014

(65) Prior Publication Data
US 2016/0040156 A1 Feb. 11, 2016

(30) Foreign Application Priority Data
Mar. 25, 2013 (GB) .................................. 1305414.3

(51) Int. Cl.
C12Q 1/68 (2018.01)
C12N 15/10 (2006.01)

(52) U.S. Cl.
CPC .............................. *C12N 15/1003* (2013.01)

(58) Field of Classification Search
None
See application file for complete search history.

(56) References Cited

U.S. PATENT DOCUMENTS

| 4,935,342 A * | 6/1990 | Seligson ............... C07H 1/08 435/270 |
| 5,728,822 A | 3/1998 | Macfarlane |
| 6,852,495 B2 * | 2/2005 | Kojima .............. C12N 15/1006 210/634 |

FOREIGN PATENT DOCUMENTS

| EP | 1820793 A1 | 8/2007 |
| EP | 2526772 A1 | 11/2012 |
| WO | 2006086271 A2 | 8/2006 |
| WO | 2009045993 A2 | 4/2009 |
| WO | WO-2009045993 A2 * | 4/2009 ............ C07F 7/1836 |
| WO | 2011107781 A1 | 9/2011 |
| WO | 2011132020 A1 | 10/2011 |
| WO | 2013175188 A1 | 11/2013 |
| WO | WO2013175188 * | 11/2013 ............. C12N 15/10 |

OTHER PUBLICATIONS

Gibson et al. (Appl Environ Microbiol, 2012, 78(9):3037-3044) (Year: 2012).*
Jing et al. (Colloid Polym Sci, 2004, 282:1089-1096) (Year: 2004).*
Isquith et al., "Surface-bonded antimicrobial activity of an organosilicon quaternary ammonium chloride," Applied Microbiology. 24(6):859-63 (1972).
Search Report for GB Application No. GB1305414.3, dated Sep. 23, 2013, 1 page.
International Search Report for Application No. PCT/GB2014050923, dated Jul. 8, 2014, 4 pages.
International Preliminary Report on Patentability for PCT/GB2014/050923, dated Oct. 8, 2015, 8 pages.

* cited by examiner

*Primary Examiner* — Stephanie K Mummert
(74) *Attorney, Agent, or Firm* — Hoffman Warnick LLC

(57) ABSTRACT

There is described a method of extracting DNA and/or RNA from a cell or capsid, the method comprising contacting the cell or capsid with a composition comprising a quaternary ammonium compound including a silicon-containing functional group. The quaternary ammonium compound may be of general formula (I) or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1. A PCR promoting agent may be provided. The method may be one of detecting and/or diagnosing a disease or medical condition.

17 Claims, No Drawings

METHOD OF DNA/RNA EXTRACTION USING SILYATED QUATERNARY AMMONIUM COMPOUNDS (SIQAC)

CROSS-REFERENCE TO RELATED APPLICATIONS

This application is the US national stage of PCT/GB2014/050923, filed 24 Mar. 2014, which claims priority to GB Patent Application No. 1305414.3, filed 25 Mar. 2013, each of which is hereby incorporated herein as though fully set forth.

The present invention relates to methods and compositions for use in DNA and/or RNA extraction.

Methods of DNA extraction are well known in the art and have several applications across diagnostics, pharmaceuticals, and research. For example, such methods are used in the genetic engineering of plants and animals, for the diagnosis of many medical conditions, in the manufacture of a number of pharmaceuticals, and in genetic fingerprinting and crime scene investigations.

Processes known in the prior art for the extraction of genetic material from a cell or capsid involve several steps. It is first necessary to achieve lysis of the cell or capsid. The DNA and/or RNA is then is dated or captured in a subsequent treatment step, purified if necessary and then released into solution for testing.

Prior art processes involve a first step in which the cell or capsid walls are broken down. This process is known as lysis. This involves disruption of the cell or capsid wall or membrane and release of the contents into the surrounding medium to create a lysate. There are several methods of cell lysis known in the art. They include physical disruption methods such as mechanical disruption, liquid homogenisation, sonication, heating, freeze/thaw cycles, and manual grinding.

However such methods have a number of drawbacks including cost, reproducibility and localised heating within a sample. Alternative methods include detergent-based cell lysis, the use of enzymes such as lysozyme and cellulase to break down the cell wall, and osmotic shock. Although it is advantageous to be able to perform lysis under chemically mild conditions, many biological cells are more difficult to disrupt and such methods are not sufficiently effective.

Along with DNA and RNA, cell or capsid lysates obtained by rupture of the membrane or wall contain many soluble (e.g. proteins) and insoluble (e.g. cell debris such as the cell wall) materials. In most prior art methods the genetic material is isolated from the other components of the cell lysate, and suitably purified. Common techniques for isolation and purification will be known to the person skilled in the art and include phenol-chloroform extraction followed by alcohol precipitation and purification by silica. Centrifugation may be carried out to remove solid material. Repeated washing and precipitation steps may be needed to achieve a sample of sufficient purity to be useful in subsequent applications. At the end of the extraction process the DNA or RNA is usually suspended in an aqueous solvent.

In many applications the isolated purified DNA or RNA is used in a PCR (polymerase chain reaction) method. PCR methods are very well known to the person skilled in the art. For many PCR techniques a sample having a high degree of purity is essential to achieve reliable results.

Problems with current methods of DNA and/or RNA extraction include the complexity of the multi-step process, the amount of time taken to complete the process, the cost of the reagents and instruments required, and the potentially low yields of DNA or RNA as material may be lost during the purification steps.

It is an aim of the present invention to provide a method of extracting DNA and/or RNA from a cell or capsid which overcomes at least one of the disadvantages of the prior art.

According to a first aspect of the present invention there is provided a method of extracting DNA and/or RNA from a cell or capsid, the method comprising contacting the cell or capsid with a composition comprising a quaternary ammonium compound including a silicon-containing functional group.

The method of the present invention may involve extraction of DNA. The method may involve the extraction of RNA. The method of the present invention may involve extraction of DNA and RNA.

The DNA and/or RNA may be extracted from any suitable cell or capsid. Capsids are the protein shells of viruses that enclose the genetic material. The virus may be any suitable virus.

The cells may be selected from prokaryotic, eukaryotic or archaeal cells. The cells may be obtained from Gram-positive or Gram-negative bacteria, mycobacteria, mycoplasma, fungi, or parasitic organisms; or from animals or plants. The cells may be animal cells, for example cells derived from humans, mammals or other animals. The cells may be plant cells. The cells may be a human or animal tissue cell. The cells may be selected from connective, muscle, nervous or epithelial tissue cells. The cells may be obtained from a bodily fluid of a human or animal, for example blood, mucus, sputum, urine, vomit or other excrement.

Exemplary Gram-negative bacteria include, but are not limited to, bacteria of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro*, and *Yersinia*. Exemplary Gram-positive bacteria include, but are not limited to, bacteria of the genera *Actinomyces, Bacillus, Clostridium, Corynebacterium, Listeria, Nocardia, Peptostreptococcus, Propionibacterium, Staphylococcus, Streptococcus*, and *Streptomyces*.

Exemplary fungal cells include any species of *Aspergillus* Exemplary yeast cells include, but are not limited to, any species of *Pichia, Saccharomyces, Schizosaccharomyces*, or *Schwanniomyces*

Parasitic cells include, but are not limited to, those belonging to the genera *Acanthamoeba, Ancylostoma, Ascaradia, Babesia, Balamuthia, Balantidium, Brugia, Clonorchis, Cryptosporidium, Dicrocoelium, Dicytocaulus, Dientamoeba, Diphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* and *Wuchereria*.

The cells may be connective tissue cells. Connective tissue cells include storage cells such as brown or white adipose cells and liver lipocytes, extracellular matrix (ECM)-secreting cells such as fibroblasts, chondrocytes, and osteoblasts, and blood/immune system cells such as lymphocytes (T lymphocytes, B lymphocytes, or plasma cells), granulocytes such as basophils, eosinophils, and neutrophils, and monocytes. The cells may be an epithelial cell. Epithelial cell types include gland cells specialized for secretion such as exocrine and endocrine glandular epithelial, and surface epithelial cells such as keratinizing and non-keratinizing surface epithelial cells. The cells may be a nervous tissue cell. Nervous tissue cells include glia cells and neurons of the central or peripheral nervous system. The cells may be muscle cells. Muscle tissue cells include skeletal, cardiac, and smooth muscle cells. Many of these cell types can be further divided. The cells may be of endodermal, mesodermal, or ectodermal origin. The cells may be stem cells or mature, differentiated cells. Exemplary stem cells include hematopoietic stem cells, neural stem cells, and mesenchymal stem cells. Exemplary mature, differentiated cell types include adipocytes such as white fat cells or brown fat cells, cardiac myocytes, chondrocytes, endothelial cells, exocrine gland cells, fibroblasts, hepatocytes, keratinocytes, macrophages, monocytes, melanocytes, neurons, neutrophils, osteoblasts, osteoclasts, pancreatic islet cells such as beta cells, skeletal myocytes, smooth muscle cells, B cells, plasma cells, T lymphocytes such as regulatory, cytotoxic, and helper, and dendritic cells.

Viruses may be a DNA virus or an RNA virus. Viruses include, but are not limited to, those of the families Adenoviridae, Arenaviradae, Arteriviridae, Ascoviridae, Asfarviridae, Astroviridae, Baculoviridae, Barnaviridae, Birnaviridae, Bornaviridae, Bromoviridae, Bunyaviridae, Caliciviridae, Caulimoviridae, Comoviridae, Coronaviridae, Chrysoviridae, Circoviridae, Closteroviridae, Cystoviridae, Dicistroviridae, Entomopoxvirinae, Filoviridae, Flaviviridae, Flexiviridae, Geminiviridae, Guttaviridae, Hepadnaviridae, Hepeviridae, Herpesviridae, Hypoviridae, Iflaviridae, Inoviridae, Iridoviridae, Leviviridae, Luteoviridae, Marnaviridae, Microviridae, Mimiviridae, Myoviridae, Nanoviridae, Narnaviridae, Nidovirales, Nimaviridae, Orthomyxoviridae, Papovaviridae, Papillomaviridae, Parvoviridae, Paramyxoviridae, Picornaviridae, Podoviridae, Polyomaviridae, Potyviridae, Poxyiridae, Pseudoviridae, Reoviridae, Retroviridae, Rhabdoviridae, Roniviridae, Rudiviridae, Sequiviridae, Siphoviridae, Tetraviridae, Togaviridae, Tombusviridae, Totiviridae and Tymoviridae. Exemplary viruses include, but are not limited to, Adenovirus, Cowpox virus, Dengue virus, Ebola virus, Epstein-Barr virus, Enterobacteria phage T4, Foot-and-mouth disease virus, Hepatitis A virus, Hepatitis B virus, Hepatitis C virus, Herpes simplex virus type 1, Herpes simplex virus type 2, Human adenovirus C, Human b-lymphotrophic virus, Human immunodeficiency virus, Human Poliovirus, Human T-cell lymphotrophic virus, Infectious hematopoietic necrosis virus, Infectious pancreatic necrosis virus, Influenza viruses types A, B, and C, ME virus, Measles virus (rubeola virus), Mengovirus, Mumps virus, Myxoma virus, Papilloma virus, Parainfluenza virus, Poliovirus, Rabies virus, Rhinovirus, Rotavirus, Rubella virus, and Yellow fever virus.

The cells or capsids may be indicative of disease. In some embodiments the cells may be cancer cells. Examples include, but are not limited to, cancers derived from brain cells, epithelial cells (carcinoma), connective tissue (sarcoma), hematopoietic cells (lymphoma and leukemia), pluripotent cells (germ cell tumour), and embryonic tissue (blastoma). In another embodiment the cells may be indicative of an autoimmune disease. Autoimmune diseases commonly affect organ and tissue types such as blood vessels, connective tissues, endocrine glands, joints, muscles, red blood cells, and the skin. Examples of autoimmune disorders include, but are not limited to, Addison's disease, celiac disease, dermatomyositis, Graves' disease, Guillan-Barre disease, inflammatory bowel disease, multiple sclerosis, pernicious anaemia, psoriasis, rheumatoid arthritis, systemic lupus erythematosus and type I diabetes. In a further embodiment the cells may be indicative of a disease that may be caused by a pathogen. The pathogen may be viral, bacterial, fungal, parasitic, or prionic.

In some embodiments the method of the present invention is used in a method of detecting and/or diagnosing a disease or medical condition.

The method of the first aspect of the present invention comprises contacting the cell or capsid with a composition comprising a quaternary ammonium compound including a silicon-containing functional group. In the method the cell or capsid may be provided in any suitable form. It may be provided as a substantially pure composition and/or it may be provided in a composition comprising one or more further components, for example one or more solvents. In some preferred embodiments the cell or capsid is provided in an aqueous composition.

In some embodiments the cell or capsid may be contained with a sample extracted from a plant or animal. For example the cell or capsid may be present in a sample of bodily fluid obtained from a human or animal. Suitable bodily fluids include blood and blood components, mucus, saliva, urine, vomit, faeces, sweat, semen, vaginal secretion, tears, pus, sputum and pleural fluid.

It is particularly advantageous that in some embodiments bodily fluid samples can be used directly in the method of the present invention. For example it is possible to carry out the method of the present invention on cells or capsids present in a whole blood sample or a sputum sample.

In the method of the first aspect of the present invention the cell or capsid is contacted with a composition comprising a quaternary ammonium compound including a silicon-containing functional group. By silicon-containing group we mean to refer to any group including a silicon atom. Preferred silicon-containing functional groups are those which include a silicon atom covalently bonded via four single bonds to four organic moieties. The silicon atom may be directly bonded to oxygen and/or carbon atoms.

Preferably the method of the first aspect of the present invention involves contacting the cells with a composition comprising a compound of general formula (I):

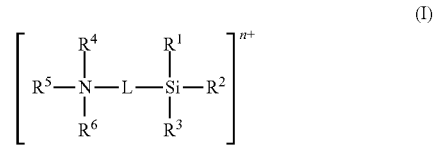

or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably $R^5$ is an alkyl group having from 8 to 30 carbon atoms, for example 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$, in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (II). This compound is commercially available as a solution in methanol.

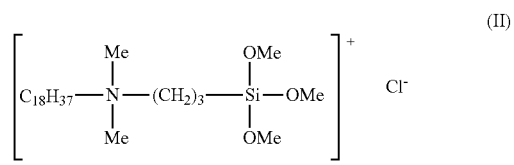

The composition contacted with the cell in the method of the first aspect may be provided in any suitable form. It may consist essentially of the quaternary ammonium compound having a silicon-containing functional group or it may comprise one or more further components. Suitably the composition includes one or more solvents. Preferred solvents are water and water miscible solvents. In embodiments in which the quaternary ammonium compound is obtained commercially as a solution in methanol, much of the methanol is suitably removed prior to use of the compound in the method of the present invention.

Preferably the composition is aqueous. In especially preferred embodiments water comprises at least 90 wt %, more preferably at least 95 wt % or at least 99 wt % of cell solvents present in the compositions. In one preferred embodiment the composition is freeze dried. In such embodiments an aqueous mixture may be provided upon contact with an aqueous composition comprising the cells or capsids. Freeze-dried compositions may be advantageous for storage and distribution.

The composition contacted with the cell or capsid in the method of the present invention preferably comprises at least 0.001 wt % of a quaternary ammonium compound including a silicon-containing functional group, preferably at least 0.01 wt %, more preferably at least 0.04 wt %, and more preferably at least 0.06 wt %.

The quaternary ammonium compound including a silicon-containing functional group preferably comprises up to 10 wt % of the composition contacted with the cell or capsid, suitably up to 5 wt %, preferably up to 1 wt %, preferably up to 0.5 wt %, more preferably up to 0.2 wt %, and more preferably up to 0.1 wt %.

The composition used in the method of the present invention may consist essentially of the compound of general formula (I) or may further include other components.

In addition to solvents mentioned above, further components may include one or more of a solubilising agent, a buffer, and a PCR promoting agent.

Preferably the composition further comprises a solubilising agent.

Suitable solubilising agents include any compound that improves the solubility, especially the solubility in water, of the quaternary ammonium compound including a silicon-containing functional group.

Examples of suitable solubilising agents include non-ionic surfactants. Non-ionic surfactants may have a hydrophilic portion, suitably an alkoxylate moiety or a sugar moiety. Suitable non-ionic surfactants include alcohol ethoxylates and fatty alcohol polyglycosides. Suitably the hydrophilic-lipophilic balance (HLB) value of a non-ionic surfactant used in the present invention is at least 7, and preferably at least 10. Especially suitable non-ionic surfactants may have an HLB value falling in the range 10-16, preferably 10-14. For the purposes of these definitions HLB value is determined by the classical method of Griffin (Griffin WC: "Calculation of HLB Values of Non-Ionic Surfactants," Journal of the Society of Cosmetic Chemists 5 (1954): 249).

Suitable solubilising agents for use herein include hydrocarbyl saccharide compounds. By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the solubilising agent is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the solubilising agent is an alkyl polyglucoside (APG), preferably a monoalkyl-polyglucoside. Suitably the solubilising agent is a compound of general formula (III):

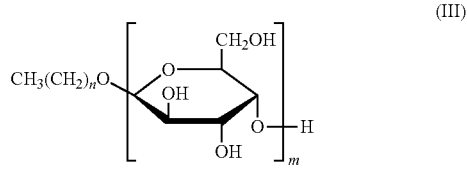

(III)

wherein n is from 5 to 12, preferably from 6 to 10, more preferably from 7 to 9 and m is from 1 to 6, preferably from 2 to 5, more preferably 3 or 4.

The solubilising agent is suitably present in the composition contacted with the cell or capsid in an amount of at least 0.001 wt %, preferably at least 0.01 wt %, more preferably at least 0.04 wt %, and more preferably at least 0.06 wt %.

The solubilising agent may be present in the composition contacted with the cell or capsid in an amount of up to 10 wt % of the composition, suitably up to 5 wt %, preferably up to 1 wt %, preferably up to 0.5 wt %, more preferably up to 0.2 wt %, and more preferably up to 0.1 wt %.

The weight ratio of the quaternary ammonium compound including a silicon-containing functional component to the solubilising.agent is preferably from 1:10 to 10:1, preferably from 1:5 to 5:1, preferably from 1:3 to 3:1, suitably from 1:2.5 to 2.5:1.

In some embodiments the weight ratio of the quaternary ammonium compound including a silicon-containing functional component to the solubilising.agent is from 1:2 to 2:1, preferably from 1:1.5 to 1.5:1, and more preferably from 1:1.2 to 1.2:1.

In some embodiments the weight ratio of the quaternary ammonium compound including a silicon-containing functional component to the solubilising.agent is from 4:1 to 1:1, preferably from 3:1 to 1.5:1, and more preferably from 2.2:1 to 1.8:1.

The composition may comprise a buffer. Any suitable buffer can be used. Preferred buffers are biologically acceptable buffers. Examples of suitable buffers include but are not limited to N-(2-acetamido)-aminoethanesulfonic acid, acetate, N-(2-acetamido)-iminodiacetic acid, 2-aminoethanesulfonic acid, ammonia, 2-amino-2-methyl-1-propanol, 2-amino-2-methyl-1,3-propanediol, N-(1,1-dimethyl-2-hydroxyethyl)-3-amino-2-hydroxypropanesulfonic acid, N,N-bis-(2-hydroxyethyl)-2-aminoethanesulfonic acid, sodium hydrogen carbonate, N,N'-bis(2-hydroxyethyl)-glycine, [bis-(2-hydroxyethyl)-imino]-tris-(hydroxymethylmethane), 1,3-bis[tris(hydroxymethyl)-methylamino]propane, boric acid, dimethylarsinic acid, 3-(cyclohexylamino)-propanesulfonic acid, 3-(cyclohexylamino)-2-hydroxyl-1-propanesulfonic acid, sodium carbonate, cyclohexylaminoethanesulfonic acid, citrate, 3-[N-bis(hydroxylethyl)amino]-2-hydroxypropanesulfonic acid, formate, glycine, glycylglycine, N-(2-hydroxyethyl)-piperazine-N'-ethanesulfonic acid, N-(2-hydroxyethyl)-piperazine-N'-3-propanesulfonic acid, N-(2-hydroxyethyl)-piperazine-N'-2-hydroxypropanesulfonic acid, imidazole, malate, maleate, 2-(N-morpholino)-ethanesulfonic acid, 3-(N-morpholino)-propanesulfonic acid, 3-(N-morpholino)-2-hydroxypropanesulfonic acid, phosphate, piperazine-N,N'-bis(2-ethanesulfonic acid), piperazine-N,N'-bis(2-hydroxypropanesulfonic acid), pyridine, succinate, 3-{[tris(hydroxymethyl)-methyl]-amino}-propanesulfonic acid, 3-[N-tris(hydroxymethyl)-methylamino]-2-hydroxypropanesulfonic acid, 2-aminoethanesulfonic acid, triethanolamine, 2-[tris(hydroxymethyl)-methylamino]-ethanesulfonic acid, N-[tris(hydroxymethyl)-methyl]-glycine, tris(hydroxymethyl)-aminomethane, One especially preferred buffer is tris(hydroxymethyl)-aminomethane (TRIS).

The composition contacted preferably has a pH of from 6.5 to 8.5, more preferably from 7 to 8.

The concentration of the buffer is suitably selected to maintain a desired pH.

In some embodiments the composition contacted with the cell or capsid in the method of the present invention includes a PCR promoting agent. A PCR promoting agent may increase the yield of the desired PCR product or decrease the production of undesired products. Examples of suitable PCR promoting agents will be known to the person skilled in the art and include betaines, DMSO, formamide, bovine serum albumin (BSA), gelatin, non-ionic detergents for example Tween®-20, NP-40, and Triton® X-100, ammonium ions, glycerol, polyethylene glycol, tetramethyl ammonium salts, and divalent metal ions. In preferred embodiments the PCR promoting agent comprises a divalent metal. Preferably the PCR promoting agent comprises $Mg^{2+}$ ions, preferably as a water salt. Most preferably the PCR promoting agent is magnesium chloride.

The PCR promoting agent is preferably present in the composition contacted with the cell or capsid in a concentration of at least 0.01 mmol, preferably at least 0.05 mmol, and more preferably at least 0.1 mmol, The PCR promoting agent may be present in the composition contacted with the cell or capsid in an amount of up to 5 mmol, suitably up to 1 mmol, preferably up to 0.5 mmol, and more preferably up to 0.3 mmol.

According to a second aspect of the present invention there is provided a composition comprising;
 (a) a quaternary ammonium compound including a silicon-containing functional group;
 (b) a solubilising agent;
 (c) a buffer; and, optionally,
 (d) a PCR promoting agent Preferred features of components (a), (b), (c) and (d) and the amounts present in the composition of the second aspect are as defined in relation to the first aspect.

An advantage of the method of the first aspect of the present invention is that the extracted DNA and/or RNA can be used for subsequent applications without the need for isolation or purification steps.

According to a third aspect of the present invention there is provided a method of identifying a component of genetic material, the method comprising the steps of:
 (a) extracting DNA and/or RNA from a cell or capsid according to the method of the first aspect; and
 (b) using the extracted DNA and/or RNA as a template in a polymerase chain reaction (PCR).

The preferred features of the third aspect are defined in the relation to the first and second aspects of the present invention.

PCR step (b) can be carried out by any means known to those skilled in the art. Suitable PCR techniques include basic PCR, reverse transcription (RT)-PCR, hot-start PCR, long PCR, quantitative endpoint PCR, quantitative real-time PCR, rapid amplified polymorphic DNA analysis, nested PCR and high-fidelity PCR.

The DNA and/or RNA used in step (b) may be in any suitable form. It may be used as a crude lysate, the supernatant of a lysate, or as isolated and purified DNA and/or RNA. In one embodiment the DNA and/or RNA is present in a supernatant. The supernatant is obtained by spinning the crude lysate in a centrifuge so that the insoluble material is pelleted to the bottom of a tube. The length of time and speed of centrifugation can be selected by the person skilled in the art.

Suitably step (b) is carried out on the mixture directly obtained following step (a). In some embodiments centrifugation may be carried out on the mixture obtained following step (a). In such embodiments the resultant supernatant may be used in step (b). This can lead to an improvement in DNA or RNA yield, and/or improved accuracy. However in preferred embodiments no further purification steps are carried out between step (a) and step (b) and satisfactory results can still be achieved.

In step (b) of the method of the third aspect of the present invention the extracted DNA and/or RNA is used as a template in PCR. As will be appreciated by the skilled person PCR techniques may be used for a number of purposes. The method of the third aspect may comprise a method of identifying a component of genetic material. In step (b) some or all of the DNA and/or RNA extracted in step (a) may be identified. Step (b) may involve confirming that a small portion of DNA and/or DNA matches a known sample. Step (b) may involve a DNA cloning step; genetic finger printing, for example in forensic applications; functional analysis of genes; diagnosis of heredity disease; and detection or diagnosis of infectious disease.

Suitably the method of the third aspect of the present invention is used in the detection of diagnosis of a disease. The method may be used to detect or diagnose, among others, genetic diseases, cancers, autoimmune diseases and pathogenic infections. Genetic markers indicative of the disease are identified in PCR step (b). A particular advantage of the present invention is that because samples containing cells or capsids do not need to be purified before or after step (a), there is a significant reduction in the time taken to reach a diagnosis.

Because the present invention can be carried out on impure samples it enables the method of the third aspect to be carried out quickly and easily and at low cost. This has significant advantages for example in the detection of diseases in less developed countries where expensive laboratory facilities are not routinely available. It is envisaged that the method of the present invention could be carried out to detect a disease on whole blood or sputum samples at mobile clinics.

A further advantage of the compositions used in the present invention is that they are highly effective at releasing DNA and/or DNA from a wide variety of cells and capsids. The present invention may provide a method by which the genetic material in a sample can be retained but in a form which is no longer active. This is potentially very useful when dealing with samples containing infectious pathogens.

According to a fourth aspect of the present invention there is provided a method of decontaminating a biological sample containing a cell or capsid, the method comprising contacting the sample with a composition comprising a quaternary ammonium compound including a silicon-containing functional group.

Preferred features of the fourth aspect are as defined in relation to the first and second aspect. The method of the fourth aspect is applicable to any suitable sample containing cells or capsids. In one exemplary embodiment, a blood sample taken from a patient suffering from malaria can be made safe by contacting the sample with the composition as the *Plasmodium* parasite is destroyed in the process. In another exemplary embodiment a blood sample taken from a patient suffering from human immunodeficiency virus would no longer pose a risk to downstream users if it had been contacted with the composition comprising a quaternary ammonium compound including a silcon-containing functional group since the capsid of the virus would be destroyed.

One advantageous feature of the fourth aspect of the present invention is that samples treated according to such a method may be transferred by regular post.

The methods and compositions of the present invention may have applications in pharmaceuticals, diagnostics, medical research, biological research, chemical research, and forensics.

The present invention will now be further described with reference to the following non-limiting examples.

EXAMPLES

The composition according to the present invention was provided as a premade aqueous solution containing 0.8 wt % of a quaternary ammonium compound including a silicon-containing functional group according to formula (II) and 1.6 wt % of a solubilising agent according to formula (III). These were provided, to form the composition, as 97% and 50% active aqueous solutions, respectively. The composition will herein be referred to as the 'PF solution'

1. DNA Purification from Blood

Three different protocols for DNA purification from blood samples were tested; the PF solution according to the present invention, osmotic shock and using the Qiagen DNeasy Blood and Tissue Kit. The extracted DNA was used in a qPCR to detect CD4 cDNA or Beta-Actin cDNA.

Examples 1-4

Direct Purification of DNA from Blood Samples with PF Solution

The aqueous PF solution was diluted to 10% v/v by the addition of 10 mM TRIS (2-amino-2-hydroxymethylpropane-1,3-diol), pH 7.5 and 0.2 mM $MgCl_2$. 5 μl of a blood sample was added to 5 μl of the diluted of PF solution and 40 μl of water. The mixture was incubated for 10 minutes at room temperature. The mixture was then spun in a centrifuge at 10,000 rpm for 10 minutes to pellet the cell debris. As a control, one sample was used directly for qPCR without the spinning step (example 3). 5 μl of the resulting supernatant (example 4), or the whole mix in the control sample, was used in a qPCR. Examples 1 and 2 were prepared by dilution of the extracted DNA 10-fold and 100-fold with water respectively, and 5 μl of these were also used in a qPCR.

Control Examples 5-6

Negative (Water) and Positive (Blood Plus DNA Template)

Comparative Examples 7-9

Purification of DNA from Blood Samples Using Osmotic Shock

5 μl of a blood sample was added to 40 μl water and 5 μl of a solution containing 10, 15 or 25 wt % NaCl. The mixture was incubated at room temperature for 10 minutes before being spun in a centrifuge at 10,000 rpm for 10 minutes to pellet the cell debris. 5 μl of the resulting supernatant was used in a qPCR.

Comparative Examples 10-13

Purification of DNA from Blood Samples Using Qiagen DNeasy Blood & Tissue Kit

DNA was extracted and purified from a 5 μl blood sample using the Qiagen DNeasy Blood and Tissue Kit following the manufacturer's standard protocol. All solutions are proprietary to Qiagen. Briefly, 20 μl proteinase K was pipetted to a 1.5 ml microcentrifuge tube. 50-100 μl of a blood sample treated with anticoagulant was added to the tube and the volume adjusted to 220 μl with PBS buffer. 200 μl Buffer AL was further added and the sample was mixed thoroughly by vortexing. The samples were incubated at 56° C. for 10 mins before 200 μl ethanol was added and mixed thoroughly by vortexing. The mixture was transferred into a DNeasy Mini spin column placed in a 2 ml collection tube and centrifuged at 8,000 rpm for 1 minute. In this way the DNA was bound to the spin column. The collection tube and flow-through were discarded. The spin column was placed in a new collection tube and the DNA was washed with 500 μl of Buffer AW1 by centrifugation at 8,000 rpm for 1 minute. An optional second wash step using 500 μl of Buffer AW2 was performed with centrifugation at 14,000 rpm for 3 minutes. 200 μl of Buffer AE was added to the spin column and was incubated at room temperature for 1 minute. The DNA was eluted from the membrane into a 1.5 ml microcentrifuge tube by centrifugation at 8,000 rpm for 1 minute. The final step was repeated to increase the DNA yield. 5 μl of the resulting extracted DNA was used in a qPCR (example 13). Examples 10-12 were made by diluting the extracted DNA 10-fold and 100-fold with water and 5 μl of these samples were used in the qPCR.

Quantitative PCR

Quantitative PCR (qPCR) was carried out. Fluorescence was plotted against the number of cycles on a logarithmic scale and a threshold for detection of DNA-based fluorescence was set at slightly above background level. The number of PCR cycles at which the fluorescence intensity exceeded the threshold was recorded. This was the cycle threshold (Ct) number and was recorded for each sample. Lower Ct numbers relate to a higher amount of extracted DNA template in the qPCR reaction.

The results of these experiments are shown in Table 1. Examples 1-4 show similar Ct numbers to examples 10-13 indicating that DNA extraction with the PF solution of the present invention shows comparable performance to DNA extraction and purification using the Qiagen DNeasy Blood and Tissue Kit but without the need for added purification steps. Osmotic shock is less effective as shown by the higher Ct numbers.

TABLE 1

| qPCR Targeting CD4 and beta-Actin cDNA | | | |
|---|---|---|---|
| Example | Sample Name | CD4 cDNA Cycle Threshold (Ct) | beta-Actin cDNA Cycle Threshold (Ct) |
| 1 | PF × $10^{-2}$ | 39.78 | 25.3 |
| 2 | PF × $10^{-1}$ | 23.83 | 23.78 |
| 3 | PF raw | 24.68 | 25.1 |
| 4 | PF spin | 15.49 | 19.49 |
| 5 | negative | — | — |
| 6 | positive | 39.22 | 39.16 |
| 7 | 25% saline | — | — |
| 8 | 15% saline | 31.32 | 39.22 |
| 9 | 10% saline | 36.6 | 39.1 |
| 10 | Qiagen × $10^{-2}$ | 40.67 | 26.57 |
| 11 | Qiagen × $10^{-1}$ (2 washes) | 23.91 | 23.88 |
| 12 | Qiagen × $10^{-1}$ | 23.55 | 24.15 |
| 13 | Qiagen | 15.01 | 25.00 |

2. Direct Isolation of HIV mRNA in De-coupled qPCR for Pyrosequencing

HIV RNA extraction from heat inactivated HIV-1 RNA positive human sera (Acrometrix) was assayed using 10% v/v PF solution in 10 mM Tris pH 7.5 and 2 mM $MgCl_2$. cDNA synthesis was performed with SuperScript III First-Strand Synthesis SuperMix, following the guideline provided by the manufacturer (Invitrogen).

HIV mRNA Extraction

5 μl of blood sample, 5 μl of diluted PF solution and 40 μl of heat inactivated HIV-1 RNA positive human serum were incubated for 10 minutes incubation at room temperature. The mixture was spun in a centrifuge for 10 minutes at 12,000 rpm to pellet the cell debris. 5 µl of the supernatant was used for cDNA synthesis.

HIV cDNA Synthesis

HIV cDNA was synthesised from the extracted HIV-1 RNA using SuperScript III First-Strand Synthesis SuperMix (Invitrogen). All solutions are proprietary to Invitrogen. 5 µl of the supernatant containing HIV-1 RNA was added to 1 µl of a gene-specific primer (2 µM aqueous stock) and 1 µl Annealing buffer in a 0.2 ml thin-walled PCR tube on ice. The mixture was made up to 8 µl with RNase/DNase-free water. The mixture was incubated at 65° C. for 5 minutes and then immediately placed on ice for 1 minute. The mixture was briefly centrifuged to collect the contents at the bottom of the tube. Whilst on ice 10 µl 2λ First—Strand Reaction Mix and 2 µl SuperScript III/RNaseOUT Enzyme Mix was added and mixed by vortexing. The mixture was incubated at 50° C. for 50 minutes. The reaction was terminated at 85° C. for 5 minutes before being chilled on ice. The resultant first-strand cDNA was used for amplification.

HIV cDNA Amplification and Pyrosequencing

Nested PCR is a modified polymerase chain reaction which is used to reduce the amount of non-specific binding. Two sets of primers are used in two successive runs of a PCR, the second set amplifying a secondary target within the amplified product of the first run. Biotools PCR mix was used. The two PCR runs were set up as follows:

Program for Nested PCR (Stage 1):

| Temperature/° C. | Time/sec | No. of Cycles |
|---|---|---|
| 94 | 300 | 1 |
| 94 | 30 | |
| 50 | 30 | 45 |
| 72 | 90 | |
| 72 | 300 | 1 |
| 10 | hold | 1 |

Program for PCR (Stage 2):

| Temperature/° C. | Time/sec | No. of Cycles |
|---|---|---|
| 95 | 300 | 1 |
| 95 | 30 | |
| 55 | 30 | 30 |
| 72 | 30 | |
| 72 | 300 | 1 |
| 10 | hold | 1 |

Pyrosequencing was performed using Qiagen Q-96 pyrosequencer running in mode SQA. The dispensation order used was 25×(A, C, T, G) priming from the sequencing oligonucleotide K103F (5'-GGAATACCACATC-CYGCAGG).

10% diluted PF solution in 10 mM TRIS pH 7.5, 2 mM MgCl2 achieved HIV RNA extraction from heat inactivated HIV-1 RNA positive human sera and subsequent cDNA synthesis with SuperScript III First-Strand Synthesis Super-Mix. Performance of both reactions was enough to obtain high quality pyrosequences, generating positive matches to existing databases in a reproducible fashion (3 repeats were performed). Therefore, the PF solution provides an extraction procedure to obtain high quality HIV-1 RNA template in sufficient amount so as to generate 100% accurate pyrosequencing. This performance surpassed those previously characterized for Speedtools RNA Virus Extraction Kit (Biotools), whose pyrosequence matching efficiency showed a maximum of 89% match.

3. Directed Isolation of *Mycobacterium tuberculosis* (MTB) gDNA for Pyrosequencing A reliable protocol was designed for the PF solution to work on *Mycobacterium tuberculosis* (MTB) cultures, balancing its purification properties and potential inhibition of PCR at high concentration. The protocol allowed extraction of high quality MTB genomic DNA (gDNA) in a sufficient amount so as to allow subsequent pyrosequencing. GeneXpert (Cepheid) was used as a comparative procedure.

Extraction of gDNA

1. Open the card and apply 20 µl of 10% PF solution diluted in 5 mM TRIS pH 7.5, 2 mM $MgCl_2$
2. Dry for 15 minutes
3. Apply 20 µl of MTB positive MGIT liquid culture available from Becton Dickinson.
4. Dry for 15 minutes
5. Punch a single disc and add to a standard PCR mix PCR and Pyrosequencing PCR was performed with the 16S-AS9 Ribosomal DNA PCR using the following cycle:

| Temperature/° C. | Time/sec | No. of Cycles |
|---|---|---|
| 95 | 30 | |
| 54 | 30 | 30 |
| 72 | 30 | |
| 72 | 300 | 1 |
| 10 | hold | 1 |

Pyrosequencing was performed using Qiagen Q-96 pyrosequencer running in mode SQA. The dispensation order used was 30×(A, C, T, G) priming from the sequencing oligonucleotide 16S-AS9.

The PF solution provided an extraction procedure which was able to obtain a high quality MTB gDNA template in sufficient amounts so as to generate 100% accurate pyrosequencing. This performance allowed mutation characterization with a higher accuracy than the rates obtained using GeneXpert (Cepheid)–(>95% specificity).

Example 14

The composition of the present invention was used to lyse cells from a variety of different organisms, according to the following procedure. In each case a culture was grown overnight in a Tryptone Soya Agar Petri dish.

One isolated colony was resuspended on 500 µl of thioglycolate liquid broth (TGG). 1 ml of $1/10^4$, $1/10^5$, $1/10^5$ and $1/10^7$ dilutions in TGG were prepared.

For the positive controls 200 µl of each dilution were taken and incubated for 10 minutes at room temperature, vortexing 3 times for 10 seconds, before spinning at 13,000 rpm for 10 minutes. 50 µl of the supernatant was plated onto a Tryptone Soya Agar Petri dish, which was then incubated at 37° C. for 18-24 h.

For the sample preparation 197 µl of each dilution was mixed with 3 µl of the test solutions and incubated for 10 minutes at room temperature, vortexing 3 times for 10 seconds during the process, before spinning at 13,000 rpm for 10 minutes. 50 µl of the supernatant was plated onto a Tryptone Soya Agar Petri dish, which was then incubated at 37° C. for 18-24 h.

In each case three test solutions were tested: the PF solution previously described in these examples, the PF solution at double concentration of each component and the PF solution at ten times dilution for each component.

The results are shown in table 2:

| Type of microorganism tested | Solid culture medium used for isolation | Reduction of viability in control medium | Reduction of viability with ARCIS treatment |
|---|---|---|---|
| *Escherichia coli* Gram-negative, facultatively anaerobic, rod-shaped bacterium | Blood Agar | NO | YES |
| *Streptococcus pneumoniae* Gram-positive, alpha-hemolytic, aerotolerant, aerobic bacterium | Blood Agar | NO | YES |
| *Staphyllococcus aureus* Gram-positive, facultative anaerobic coccal bacterium | Blood Agar | NO | YES |
| *Bacillus cereus* Gram-positive, rod-shaped, beta hemolytic bacterium | Blood Agar | NO | YES |
| *Candida albicans* diploid fungus that grows both as yeast and filamentous cells | Saboraud Dextrose Agar | NO | YES |

These results show that treatment according to the present invention can achieve cell lysis on a range of different organisms.

The invention claimed is:

1. A method of extracting DNA and/or RNA from a cell or capsid, the method comprising contacting the cell or capsid with a composition comprising a quaternary ammonium compound including a silicon-containing functional group of general formula (I):

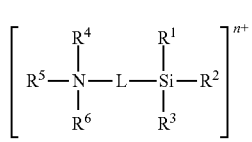

(I)

or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1; and wherein the composition is aqueous or dried.

2. A method according to claim 1 wherein the DNA and/or RNA is extracted from prokaryotic, eukaryotic or archaeal cells.

3. A method according to claim 1 wherein the cells are obtained from Gram-positive or Gram-negative bacteria, mycobacteria, mycoplasma, fungi, or parasitic organisms; or from animals or plants.

4. A method according to claim 3 wherein the cells are selected from Gram-negative bacteria of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro*, or *Yersinia*, or from Gram-positive bacteria of the genera *Actinomyces, Bacillus, Clostridium, Corynebacterium, Listeria, Nocardia, Peptostreptococcus, Propionibacterium, Staphylococcus, Streptococcus*, or *Streptomyces*.

5. A method according to claim 1 wherein the capsid is selected from a virus of the families Adenoviridae, Arenaviradae, Arteriviridae, Ascoviridae, Asfarviridae, Astroviridae, Baculoviridae, Barnaviridae, Birnaviridae, Bornaviridae, Bromoviridae, Bunyaviridae, Caliciviridae, Caulimoviridae, Comoviridae, Coronaviridae, Chrysoviridae, Circoviridae, Closteroviridae, Cystoviridae, Dicistroviridae, Entomopoxvirinae, Filoviridae, Flaviviridae, Flexiviridae, Geminiviridae, Guttaviridae, Hepadnaviridae, Hepeviridae, Herpesviridae, Hypoviridae, Iflaviridae, Inoviridae, Iridoviridae, Leviviridae, Luteoviridae, Marnaviridae, Microviridae, Mimiviridae, Myoviridae, Nanoviridae, Narnaviridae, Nidovirales, Nimaviridae, Orthomyxoviridae, Papovaviridae, Papillomaviridae, Parvoviridae, Paramyxoviridae, Picornaviridae, Podoviridae, Polyomaviridae, Potyviridae, Poxyiridae, Pseudoviridae, Reoviridae, Retroviridae, Rhabdoviridae, Roniviridae, Rudiviridae, Sequiviridae, Siphoviridae, Tetraviridae, Togaviridae, Tombusviridae, Totiviridae or Tymoviridae.

6. A method according to claim 1 wherein the capsid is from a virus selected from a group consisting of: Adenovirus, Cowpox virus, Dengue virus, Ebola virus, Epstein-Barr virus, Enterobacteria phage T4, Foot-and-mouth disease virus, Hepatitis A virus, Hepatitis B virus, Hepatitis C virus, Herpes simplex virus type 1, Herpes simplex virus type 2, Human adenovirus C, Human b-lymphotrophic virus, Human immunodeficiency virus, Human Poliovirus, Human T-cell lymphotrophic virus, Infectious hematopoietic necrosis virus, Infectious pancreatic necrosis virus, Influenza viruses types A, B, and C, ME virus, Measles virus (rubeola virus), Mengovirus, Mumps virus, Myxoma virus, Papilloma virus, Parainfluenza virus, Poliovirus, Rabies virus, Rhinovirus, Rotavirus, Rubella virus, and Yellow fever virus.

7. A method according to claim 1 wherein the cells or capsids are indicative of disease or of a disease caused by a pathogen.

8. A method according to claim 1 wherein the cell or capsid is provided in a composition comprising a solvent.

9. A method according to claim 1, wherein the quaternary ammonium compound including a silicon-containing functional group is a compound of general formula (II)

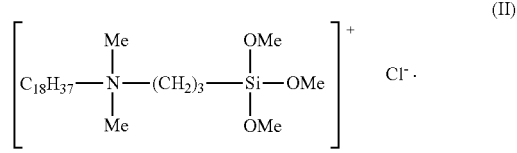

(II)

10. A method according to claim 1 wherein the composition contacted with the cell or capsid comprises from 0.001 wt % to 10 wt % of the quaternary ammonium compound including a silicon-containing functional group.

11. A method according to claim 1 wherein the composition comprises a solubilising agent.

12. A method according to claim 11 wherein the solubilising agent is an alkyl polyglucoside (APG) of general formula (III):

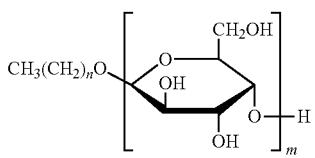
(III)

wherein n is from 5 to 12, preferably from 6 to 10, more preferably from 7 to 9 and m is from 1 to 6, preferably from 2 to 5, more preferably 3 or 4.

13. A method according to claim 11 wherein the composition contacted with the cell or capsid comprises from 0.001 wt % to 10 wt % of a solubilising agent.

14. A method according to claim 1 wherein the composition contacted with the cell or capsid includes a PCR promoting agent, selected from a group consisting of: betaines, DMSO, formamide, bovine serum albumin (BSA), gelatin, non-ionic detergents, ammonium ions, glycerol, polyethylene glycol, tetramethyl ammonium salts, and divalent metal ions.

15. A method according to claim 14 wherein the PCR promoting agent is present in the composition contacted with the cell or capsid in a concentration of from 0.01 mmol to 5 mmol.

16. A method of identifying a component of genetic material, the method comprising the steps of:
(a) extracting DNA and/or RNA from a cell or capsid according to the method of claim 1; and
(b) using the extracted DNA and/or RNA as a template in a polymerase chain reaction (PCR).

17. A method according to claim 16 wherein the DNA and/or RNA used in step (b) may be used as a crude lysate, the supernatant of a lysate, or as isolated and purified DNA and/or RNA and step (b) is carried out on the mixture directly obtained following step (a).

* * * * *